United States Patent
Kwon et al.

(10) Patent No.: US 9,394,262 B2
(45) Date of Patent: Jul. 19, 2016

(54) METHOD OF SEPARATING CARBON NANOTUBES

(71) Applicants: Samsung Electronics Co., Ltd., Suwon-si, Gyeonggi-do (KR); Gachon University of Industry-Academic Cooperation Foundation, Seongnam-si, Gyeonggi-do (KR)

(72) Inventors: Tae-Yong Kwon, Suwon-si (KR); Woo-Jae Kim, Seoul (KR); Hyung-Sam Kim, Suwon-si (KR)

(73) Assignees: SAMSUNG ELECTRONICS CO., LTD. (KR); GACHON UNIVERSITY OF INDUSTRY-ACADEMIC COOPERATION FOUNDATION (KR)

( * ) Notice: Subject to any disclaimer, the term of this patent is extended or adjusted under 35 U.S.C. 154(b) by 324 days.

(21) Appl. No.: 13/973,985

(22) Filed: Aug. 22, 2013

(65) Prior Publication Data

US 2014/0066631 A1 Mar. 6, 2014

(30) Foreign Application Priority Data

Aug. 29, 2012 (KR) ........................ 10-2012-0095169

(51) Int. Cl.
*C07D 249/04* (2006.01)
*C01B 31/02* (2006.01)
*B82Y 10/00* (2011.01)

(52) U.S. Cl.
CPC ............... *C07D 249/04* (2013.01); *B82Y 10/00* (2013.01); *C01B 31/0266* (2013.01)

(58) Field of Classification Search
CPC .......................... C07D 249/04; C01B 31/0266
See application file for complete search history.

(56) References Cited

U.S. PATENT DOCUMENTS

| 7,387,735 | B2 | 6/2008 | Park et al. |
| 7,488,876 | B2 | 2/2009 | Jung et al. |
| 7,641,883 | B2 | 1/2010 | Shin et al. |
| 7,884,300 | B2 | 2/2011 | Akasaka et al. |
| 7,887,774 | B2 | 2/2011 | Strano et al. |
| 7,939,047 | B2 | 5/2011 | Tour et al. |
| 2006/0278579 | A1 | 12/2006 | Choi et al. |
| 2009/0020732 | A1 | 1/2009 | Shin et al. |
| 2012/0039790 | A1 | 2/2012 | Sandhu |

FOREIGN PATENT DOCUMENTS

| JP | 2008266111 A | 11/2008 |
| JP | 2009132604 A | 6/2009 |
| JP | 2012036041 A | 2/2012 |
| KR | 20070098433 A | 10/2007 |
| KR | 20100025113 A | 3/2010 |
| KR | 20100114242 A | 10/2010 |
| KR | 20110117321 A | 10/2011 |
| KR | 20110139916 A | 12/2011 |

OTHER PUBLICATIONS

Kolb et al. "Click Chemistry: Diverse Chemical Function from a Few Good Reactions" Angewandte Chemie Internation Edition, 2001, vol. 40, pp. 2004-2021.*
Voggu et al. "A Simple Method of Separating Metallic and Semiconducting Single-Walled Carbon Nanotubes Based on Molecular Charge Transfer" Journal of the American Chemical Society, 2010, vol. 132, pp. 5560-5561.*

\* cited by examiner

*Primary Examiner* — Joseph Kosack
(74) *Attorney, Agent, or Firm* — Renaissance IP Law Group LLP (57) ABSTRACT

Provided is a method of separating carbon nanotubes, the method comprising: forming first carbon nanotubes having a first functional group, forming a substrate having a second functional group, and causing the first carbon nanotubes to adhere to the substrate by a click chemistry reaction between the first functional group and the second functional group.

8 Claims, 6 Drawing Sheets

METHOD OF SEPARATING CARBON NANOTUBES

This application claims priority from Korean Patent Application No. 10-2012-0095169 filed on Aug. 29, 2012 in the Korean Intellectual Property Office, the disclosure of which is incorporated herein by reference in its entirety.

BACKGROUND

1. Technical Field

The present disclosure relates to a method of separating carbon nanotubes.

2. Description of the Related Art

The carbon nanotube (CNT) is a compound in which carbon atoms are bonded to each other in a hexagonal, honeycomb pattern to form a tube shape. Carbon nanotubes have very high anisotropy and have various structures such as single-walled, multi-walled, and bundled structures. Carbon nanotubes are nanomaterials on the scale of nanometers (nm=one billionth of a meter) and exhibit superior mechanical properties, electrical selectivity, excellent field-emission properties, and highly efficient hydrogen storage properties.

Furthermore, carbon nanotubes exhibit characteristics of a semiconductor or metal depending on how the hexagonal honeycomb of carbon atoms is arranged (rolled). The energy gap of the carbon nanotube varies according to the diameter of the tube, and the quasi-one-dimensional energy structure of the carbon nanotube allows the carbon nanotube to have unusual quantum effects.

Carbon nanotubes can be synthesized by various methods such as arc discharge, pyrolysis, laser ablation, plasma enhanced chemical vapor deposition (PECVD), thermal chemical vapor deposition, and electrolysis. At the stage of synthesis, carbon nanotubes exist mostly in the form of bundles. Therefore, to fully utilize superior mechanical and electrical properties of carbon nanotubes, it is important to separate and disperse the carbon nanotubes one by one. Moreover, carbon nanotubes exist as a mixture of carbon nanotubes with metallic characteristics and carbon nanotubes with semiconducting characteristics. Therefore, it is desirable to isolate different carbon nanotubes that serve different purposes. For example, only metallic carbon nanotubes are used for an electrode to increase the conductivity of the electrode. In addition, only semiconducting carbon nanotubes are used for the semiconductor layer of a transistor. In this regard, various studies are being conducted to efficiently separate carbon nanotubes with desired characteristics from other carbon nanotubes.

SUMMARY

Aspects of the present disclosure provide a method of separating certain carbon nanotubes from a mixture of carbon nanotubes using a click chemistry reaction.

However, aspects of the present disclosure are not restricted to the one set forth herein. The above and other aspects of the present disclosure will become more apparent to one of ordinary skill in the art to which the present disclosure pertains by referencing the detailed description of the present disclosure given below.

According to an aspect of the present disclosure, there is provided a method of separating carbon nanotubes, the method comprising: forming first carbon nanotubes that have a first functional group, forming a substrate that has a second functional group, and adhering the first carbon nanotubes to the substrate by a click chemistry reaction between the first functional group and the second functional group.

According to another aspect of the present disclosure, there is provided a method of separating carbon nanotubes, the method comprising: forming a first mixture of metallic carbon nanotubes and semiconducting carbon nanotubes, attaching an alkyne functional group to the metallic carbon nanotubes by adding a first compound to the first mixture, forming a substrate having an azide functional group attached thereto, and letting the metallic carbon nanotubes bond to the substrate by triazole formed by a chemical reaction between the alkyne functional group and the azide functional group.

BRIEF DESCRIPTION OF THE DRAWINGS

The above and other aspects and features of the present disclosure will become more apparent by describing in detail exemplary embodiments thereof with reference to the attached drawings, in which.

DETAILED DESCRIPTION OF THE EMBODIMENTS

The present disclosure will now be described more fully hereinafter with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art. The same reference numbers indicate the same components throughout the specification. In the attached figures, the thickness of layers and regions is exaggerated for clarity.

It will be understood that when an element or layer is referred to as being "connected to," or "coupled to" another element or layer, it can be directly connected to, or coupled to, another element or layer, or to whatever intervening elements or layers that may be present. In contrast, when an element is referred to as being "directly connected to" or "directly coupled to" another element or layer, there are no intervening elements or layers present. Like numbers refer to like elements throughout. As used herein, the term "and/or" includes any and all combinations of one or more of the associated listed items.

It will also be understood that when a layer is referred to as being "on" another layer or substrate, it can be directly on the other layer or substrate, but intervening layers may also be present. In contrast, when an element is referred to as being "directly on" another element, there are no intervening elements present.

It will be understood that, although the terms first, second, etc. may be used herein to describe various elements, these elements should not be limited by these terms. These terms are only used to distinguish one element from another element. Thus, for example, a first element, a first component or a first section discussed below could be termed a second element, a second component or a second section without departing from the teachings of the present disclosure.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Unless defined otherwise, all technical and scientific terms used herein have the same meaning as commonly understood by one of ordinary skill in the art to which this invention belongs. It is noted that the use of any and all examples, or exemplary terms provided herein is intended merely to better illuminate the invention and is not a limitation on the scope of the invention unless otherwise specified. Further, unless defined otherwise, all terms defined in generally used dictionaries may not be overly interpreted.

A method of separating carbon nanotubes according to an embodiment of the present disclosure will now be described with reference to FIGS. 1 through 6B.

Figure 1:
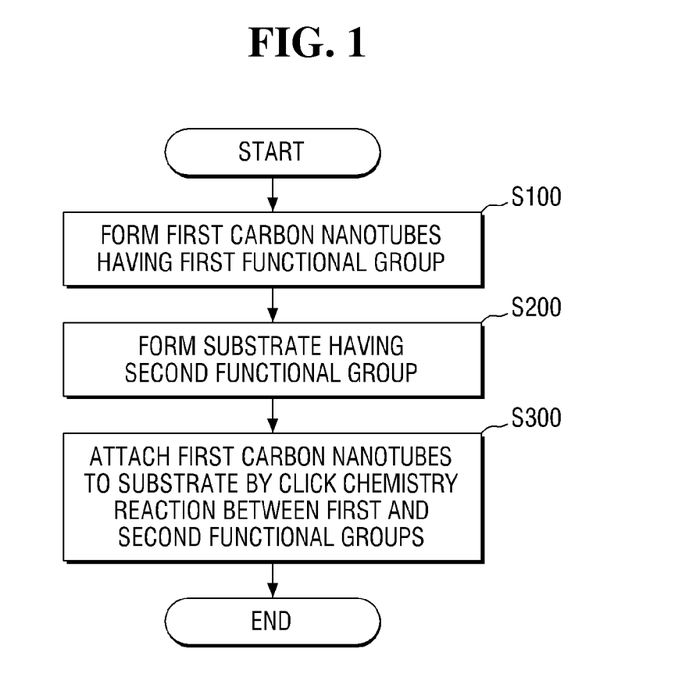
FIG. 1 is a flowchart illustrating a method of separating carbon nanotubes according to an embodiment of the present disclosure.
Figure 2:
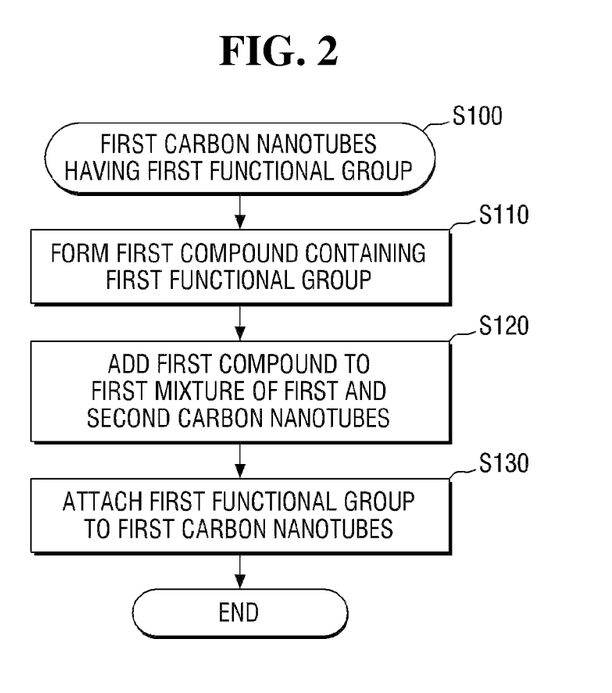
FIG. 2 is a flowchart illustrating operation S100 of FIG. 1.
Figure 3A:
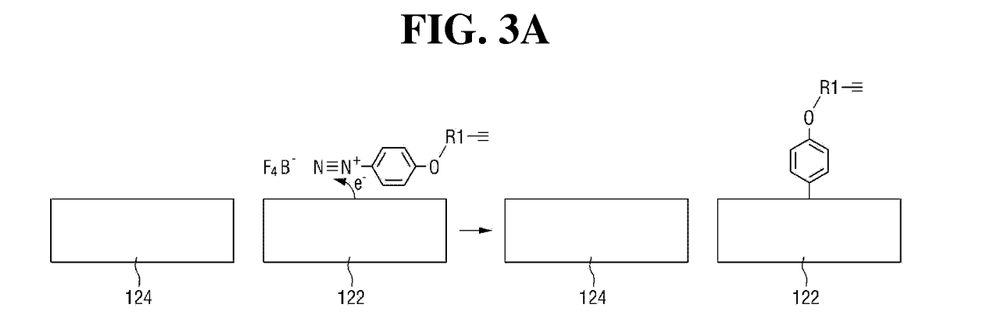
FIGS. 3A and 3B are diagrams illustrating a process of FIG. 2 in which a first functional group is attached to first carbon nanotubes.
Figure 3B:
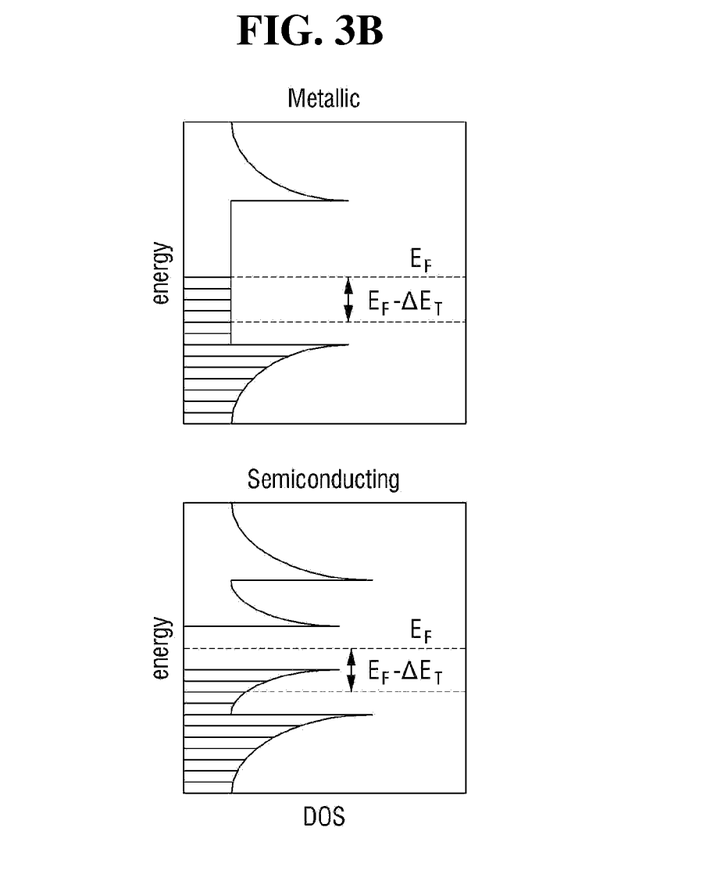
Figure 4:
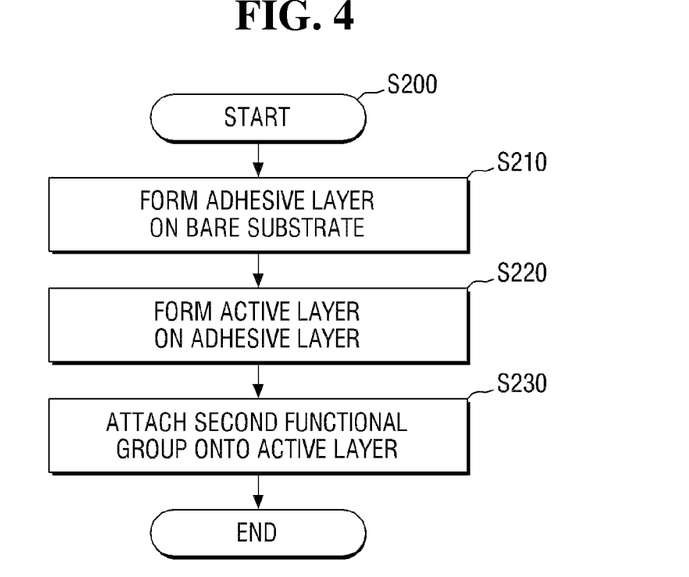
FIG. 4 is a flowchart illustrating operation S200 of FIG. 1.
Figure 5:
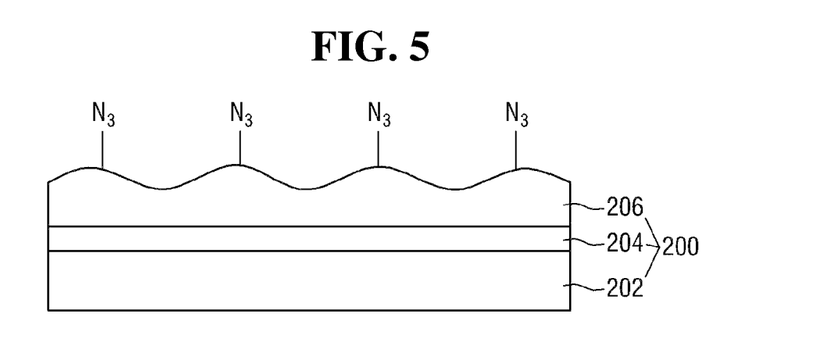
FIG. 5 is a diagram illustrating a substrate obtained by the process of FIG. 4.
Figure 6A:
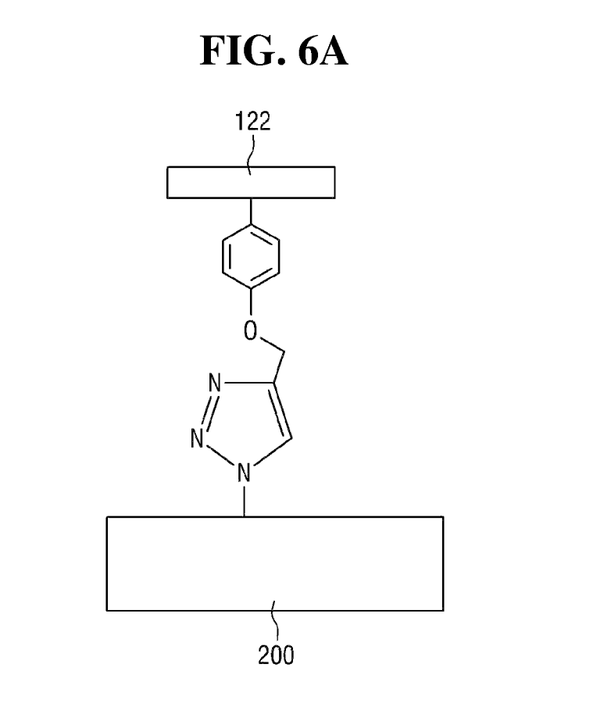
FIGS. 6A and 6B are diagrams illustrating operation S300 of FIG. 1.
Figure 6B:
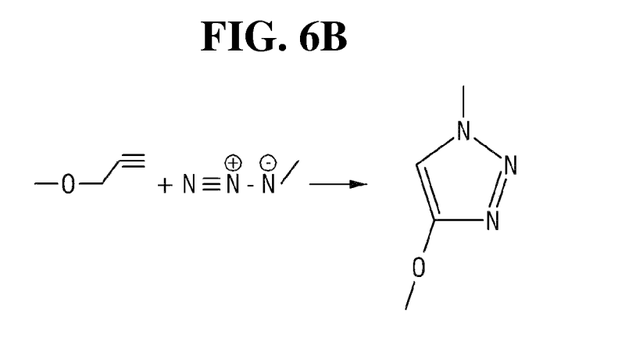

FIG. 1 is a flowchart illustrating a method of separating carbon nanotubes according to an embodiment of the present disclosure. FIG. 2 is a flowchart illustrating operation S100 of FIG. 1. FIGS. 3A and 3B are diagrams illustrating a process of FIG. 2 in which a first functional group is attached to first carbon nanotubes. FIG. 4 is a flowchart illustrating operation S200 of FIG. 1. FIG. 5 is a diagram illustrating a substrate obtained by the process of FIG. 4. FIGS. 6A and 6B are diagrams illustrating operation S300 of FIG. 1.

Referring to FIGS. 1 through 3B, first carbon nanotubes 122 having a first functional group may be formed (operation S100). In other words, the first carbon nanotubes 122 having the first functional group attached thereto may be formed.

The first functional group may be, e.g., an alkyne group. In the embodiment of the present disclosure, the first functional group may be connected to the first carbon nanotubes 122 via another compound. However, the present disclosure is not limited thereto. That is, the first functional group can be directly connected to the first carbon nanotubes 122. In some embodiments, the first functional group may be the alkyne group. The first carbon nanotubes 122 may be, e.g., metallic carbon nanotubes. That is, the first carbon nanotubes 122 may have an armchair-type structure and have no band gap or a very small band gap. Thus, the first carbon nanotubes 122 may exhibit properties substantially identical to those of metal.

The forming of the first carbon nanotubes 122 having the first functional group will now be described in greater detail.

Referring to FIG. 2, a first compound containing the first functional group may be formed (operation S110). In some embodiments, the first compound may additionally contain a second functional group. The second functional group contained in the first compound may be a functional group which reacts well with the first carbon nanotubes 122.

In some embodiments, it is assumed that the first carbon nanotubes 122 are metallic carbon nanotubes. Therefore, the first compound may be described based on the assumption that the first carbon nanotubes 122 are metallic carbon nanotubes. As described above, the first functional group contained in the first compound may be the alkyne group. The second functional group contained in the first compound may be a functional group which reacts well with metallic carbon nanotubes, for example, a diazo group (N=2). That is, the first compound may contain the diazo group and the alkyne group. Specifically, the first compound may be alkynephenyldiazonium (formula 1). The alkyne group of the first compound may be bonded at the position of a para-substituent of diazonium.

(1)

An oxygen-R1 bond may be located between the alkyne group and the diazonium of the first compound. Here, R1 may be an organic compound with 1 to 10 carbons, preferably, an organic compound with 1 to 3 carbons. The reason why R1 with a smaller number of carbons is preferred may be related to reactivity of the first functional group. Oxygen is a material with a high electron affinity. That is, oxygen tends to strongly attract electrons around it. If oxygen is located around the alkyne group having a triple carbon bond, electrons that form the triple bond may be distributed toward the oxygen. On the other hand, as the distance from oxygen increases, the distribution of electrons decreases. Thus, the alkyne group, when located far away from oxygen, exhibits strong reactivity. Therefore, if R1 containing a small number of carbons is located between the alkyne group and the diazonium of the first compound, the reactivity of the alkyne group may increase.

In the following description of the embodiment of the present disclosure, it will be assumed that the number of carbons contained in R1 of the first compound is one.

Referring to FIG. 2, the first compound may be added to a first mixture of the first carbon nanotubes 122 and second carbon nanotubes 124 (operation S120). That is, after the first mixture of the first carbon nanotubes 122 and the second carbon nanotubes 124 is formed, the first compound may be mixed with the first mixture.

The first carbon nanotubes 122 contained in the first mixture may be metallic carbon nanotubes, and the second carbon nanotubes 124 contained in the first mixture may be semiconducting carbon nanotubes. The first carbon nanotubes 122 may include semi-metallic carbon nanotubes.

As described above in Description of the Related Art, carbon nanotubes can be synthesized by various methods such as arc discharge, pyrolysis, laser ablation, plasma enhanced chemical vapor deposition (PECVD), thermal chemical vapor deposition, and electrolysis. However, carbon nanotubes formed by these methods have heterogeneity, that is, have various diameters and chiralities and various electronic structures. For example, the carbon nanotubes may include single-walled carbon nanotubes, multi-walled carbon nanotubes, double-walled carbon nanotubes, bucky tubes, fullerene tubes, tubular fullerenes, graphite fiber, and a combination of the same. The first mixture containing such various types of carbon nanotubes is formed. Therefore, the first mixture containing the first carbon nanotubes 122 and the second carbon nanotubes 124 can be formed.

A first mixed solution containing the first mixture may be formed. The first compound is added to the first mixed solution. The first mixed solution may further contain a dispersant. In some embodiments, after the first compound is formed, the first mixed solution is formed. Then, the first compound is added to the first mixed solution. However, the present disclosure is not limited thereto. That is, after the first mixed solution which contains the first mixture of the first carbon nanotubes 122 and the second carbon nanotubes 124 is formed, the first compound may be formed and then added to the first mixed solution. Alternatively, the first mixture and the first compound may be simultaneously put into a solvent material.

Specifically, the first mixed solution which contains the first mixture of metallic carbon nanotubes and semiconducting carbon nanotubes is formed. A carbon nanotube dispersant may further be added to the first mixed solution. The carbon nanotube dispersant may help the carbon nanotubes be dispersed uniformly without tangling with each other. The carbon nanotube dispersant may uniformly disperse the metallic carbon nanotubes, thereby increasing reaction area. In other words, in the first mixed solution containing the carbon nanotube dispersant, the first carbon nanotubes 122 and the second carbon nanotubes 124 may be homogenized. Thus, some of the carbon nanotubes may be capsulated into a micellar-like assembly. Alkynephenyldiazonium, which may be the first compound, may be added to the first mixed solution having the carbon nanotube dispersant added therein.

To facilitate the dispersion of the carbon nanotubes, a surfactant may further be added to the first mixed solution. Examples of the surfactant include, but are not limited to, an ionic surfactant, a nonionic surfactant, a cationic surfactant, or an anionic surfactant.

Referring to FIGS. 2 through 3B, the first functional group may be attached to the first carbon nanotubes 122 (operation S130). In other words, the first compound and the first carbon nanotubes 122 may react with each other, thereby forming the first carbon nanotubes 122 having the first functional group.

The second functional group contained in the first compound is removed from the first compound by a chemical reaction with the first carbon nanotubes 122. That is, the first compound (represented by formula 1) excluding the diazo group is bonded to the first carbon nanotubes 122. However, since the second functional group contained in the first compound does not react with the second carbon nanotubes 124, the first functional group is not bonded to the second carbon nanotubes 124. Therefore, in the first mixed solution containing various types of carbon nanotubes, only the first carbon nanotubes 122 are bonded to the first functional group, and the other carbon nanotubes remain unbonded to the first functional group.

Specifically, referring to FIG. 3A, the first compound of formula 1 extracts electrons from the first carbon nanotubes 122. The diazo group of the first compound which receives the extracted electrons is separated from a benzene ring of the first compound and then released as a nitrogen (N2) gas. The benzene ring without the diazo group is covalently bonded to the first carbon nanotubes 122. That is, a C—C covalent bond is formed between the benzene ring of the first compound and the first carbon nanotubes 122. As a result, the first compound without the diazo group remains on the surface of the first carbon nanotubes 122. Therefore, the first functional group is bonded to the first carbon nanotubes 122, and the first carbon nanotubes 122 having the first functional group are formed as a result.

Referring to FIG. 3B, metallic carbon nanotubes have a higher electron density around a Fermi energy level $E_F$ than semiconducting carbon nanotubes. In other words, the metallic carbon nanotubes have a higher electron density than the semiconducting carbon nanotubes in a range from $E_F$ to $E_F$–$E_T$ in which electrons contained in carbon nanotubes can be involved in an oxidation-reduction reaction of the carbon nanotubes and the first compound. A high electron density around the Fermi energy level indicates that a large number of electrons can participate in initial activation. The metallic carbon nanotubes with a high electron density around the Fermi energy level may show a higher chemical activity than the semiconducting carbon nanotubes with a low electron density around the Fermi energy level. Therefore, the diazo group, which is the second functional group contained in the first compound, may receive electrons only from the first carbon nanotubes 122 which are metallic carbon nanotubes. The diazo group of the first compound which receives the electrons is released as a nitrogen gas, and the remainder of the first compound is chemically bonded to the first carbon nanotubes 122.

Referring to FIGS. 1, 4 and 5, a substrate 200 having a third functional group may be formed (operation S200).

Specifically, a substrate having the third functional group may be formed by attaching the third functional group onto a bare substrate 202 (operation S230). If the third functional group does not adhere well to the bare substrate 202, an active layer 206 may further be formed on the bare substrate 202 (operation S220). Before the active layer 206 is formed on the bare substrate 202, an adhesive layer 204 may further be formed on the bare substrate 202 (operation S210). That is, the bare substrate 202, the adhesive layer 204, and the active layer 206 may be stacked sequentially, and then the third functional group may be bonded onto the active layer 206. Through the above process, the substrate 200 having the third functional group may be formed. That is, when it is difficult to bond the third functional group onto the bare substrate 202, the active layer 206 and the adhesive layer 204 may additionally be formed.

The bare substrate 202 may be, e.g., a transparent substrate, specifically, a rigid substrate, such as a quartz substrate or a glass substrate, or a flexible plastic substrate such as a transparent plastic substrate. The transparent plastic substrate may be, but is not limited to, polyimide, polyethyleneterephthalate (PET), polyethylene naphthalate (PEN), polymethylmethacrylate (PMMA), polycarbonate (PC), polyethersulfone (PES), or polyester.

In some embodiments, the third functional group may be an azide group (—N=N+=N—). In addition, in some embodiments, the bare substrate 202 may be, but is not limited to, a glass substrate.

In some embodiments, the adhesive layer 204 and the active layer 206 are stacked sequentially on the bare substrate 202, and then the third functional group is attached onto the active layer 206. However, the present disclosure is not limited thereto. That is, if a bond is formed between the third functional group and the bare substrate 202 since the third functional group adheres well to the bare substrate 202, the adhesive layer 204 and the active layer 206 may not be formed. If the third functional group does not easily adhere to the bare substrate 202, at least one of the adhesive layer 204 or the active layer 206 may be formed between the bare substrate 202 and the third functional group. In this case, the formed layer may be a layer to which the third functional group can adhere well and which can adhere to the bare substrate 202. In other words, the materials that form the bare substrate 202, the adhesive layer 204 and the active layer 206 may determine the cross-sectional structure of the substrate 200 having the third functional group.

Referring to FIG. 4, the adhesive layer 204 may be formed on the bare substrate 202 (operation S210). The adhesive layer 204 may contain a material that can increase the bond between the active layer 206, which is to be formed later, and the bare substrate 202. The adhesive layer 204 may be, but is not limited to, polyethyleneimine (PEI). The adhesive layer 204 may vary according to the types of the bare substrate 202 and the active layer 206.

Specifically, a PEI aqueous solution is prepared by mixing PEI with a dispersant in deionized (DI) water. Then, the bare substrate 202 is immersed in the PEI aqueous solution. As a result of immersing the bare substrate 202 in the PEI aqueous solution, the adhesive layer 204 may be formed on the bare substrate 202. The area of the adhesive layer 204 formed on the bare substrate 202 may be adjusted in view of the area of the third functional group which is to be formed on the adhesive layer 204.

Referring to FIG. 4, the active layer 206 may be formed on the adhesive layer 204 (operation S220). The third functional group may be attached onto the active layer 206 (operation S230). The active layer 206 may be a layer that helps the third functional group bond to the bare substrate 202. In other words, the active layer 206 may increase the surface area of the bare substrate 202 on which a chemical reaction can occur, thereby helping the third functional group readily adhere onto the bare substrate 202. The active layer 206 may contain a polymer compound, specifically, polyacrylic acid.

In some embodiments, a chemical substance that contains the third functional group may be azide.

Specifically, a second mixed solution of azide and a polymer compound is formed. The second mixed solution may be a solution having the azide and the polymer compound added in DI water. Therefore, the azide and the polymer compound may be mixed evenly in the DI water. To mix the azide and the polymer compound more evenly, the second mixed solution may further contain a dispersant. Here, the term "azide" may refer to a compound containing the azide group, more specifically, an organic compound containing the azide group.

The bare substrate 202 may be immersed in the second mixed solution. Specifically, the bare substrate 202 having the adhesive layer 204 may be immersed in the second mixed solution. When the bare substrate 202 is immersed in the second mixed solution, the active layer 206 is formed on the adhesive layer 204. In addition, the third functional group may be attached onto the bare substrate 202 having the active layer 206. Through the above process, the substrate 200 having the third functional group may be formed. The active layer 206 may be formed on the adhesive layer 204 by the polymer compound contained in the second mixed solution. Specifically, the active layer 206 may be a layer that contains polyacrylic acid. The third functional group attached onto the active layer 206 may be formed by the azide contained in the second mixed solution.

In some embodiments, the forming of the active layer 206 on the adhesive layer 204 and the attaching of the third functional group onto the active layer 206 may occur in the same process. However, the present disclosure is not limited thereto. The forming of the active layer 206 on the adhesive layer 204 and the attaching of the third functional group onto the active layer 206 can occur in different processes. That is, after the process of forming the active layer 206 on the adhesive layer 204 of the bare substrate 202 is performed, the process of attaching the third functional group onto the active layer 206 may be performed.

Referring to FIG. 5, the substrate 200 includes the bare substrate 202, the adhesive layer 204, the active layer 206, and the third functional group. If the third functional group does not bond well with the bare substrate 202, the adhesive layer 204 and/or the active layer 206 may be interposed between the third functional group and the bare substrate 202. The third functional group may be directly bonded to the active layer 206. However, the present disclosure is not limited thereto. That is, the third functional group can be bonded to the active layer 206 via another chemical substance, for example, an organic chemical substance.

A surface of the active layer 206 to which the third functional group is bonded may be uneven. The uneven surface of the active layer 206 has the effect of increasing a chemical reaction area between the chemical substance containing the third functional group and the active layer 206. Therefore, the active layer 206 having the uneven surface enables the third functional group to easily adhere onto the bare substrate 202. In the drawing, the surface of the active layer 206 is shaped like a sine wave. However, the shape of the surface of the active layer 206 is not limited to the sine wave. The shape of the surface of the active layer 206 can vary according to the type of material contained in the active layer 206.

In some embodiments, the active layer 206 having an uneven surface is formed in order to increase the surface to which the third functional group can be bonded. However, the present disclosure is not limited thereto. For example, a surface of the bare substrate 202 to which the third functional group is bonded can be treated to form grooves or trenches in the surface of the bare substrate 202. In addition, the bare substrate 202 which easily reacts with the chemical substance containing the third functional group may be used as described above.

Referring to FIGS. 1, 6A and 6B, the first carbon nanotubes 122 having the first functional group may be attached to the substrate 200 having the third functional group. The first carbon nanotubes 122 may be attached to the substrate 200 by a click chemistry reaction between the first functional group and the third functional group (operation S300). Since only the first carbon nanotubes 122 are bonded onto the substrate 200, they can be separated from other carbon nanotubes. "Click chemistry" generally makes it possible for certain chemical building blocks to "click" together in an irreversible linkage and, in the present disclosure, may embody versatile cycloaddition reactions between azides and alkynes that enable a number of useful applications.

The click chemistry reaction occurs between the alkyne group which is the first functional group contained in the first carbon nanotubes 122 and the azide group which is the third functional group attached onto the substrate 200. For the click chemistry reaction between the first functional group and the third functional group, a catalyst may be used. The click chemistry reaction between the first functional group and the third functional group results in the formation of a second compound. The second compound formed by the click chemistry reaction may be triazole ($C_2H_3N_3$) (represented by a dotted box in FIG. 6A).

As described above, the first functional group may be the alkyne group, and the third functional group may be the azide group. The process in which only metallic carbon nanotubes (i.e., the first carbon nanotubes 122) are attached to the substrate 200 will now be described in detail.

The substrate 200 having the third functional group attached thereto is immersed in the first mixed solution of the second carbon nanotubes 124 and the first carbon nanotubes 122 having the first functional group. In addition, a catalyst for the click chemistry reaction is added to the first mixed solution having the substrate 200 immersed therein. In some embodiments, instead of immersing the substrate 200 in the first mixed solution, other methods of making the substrate in contact with the mixed solution for the click chemistry reaction within the spirit and scope of the present disclosure. For example, the first mixed solution may be sprayed onto the substrate 200. Here, the "click chemistry reaction" refers to an azide-alkyne huisgen cycloaddition reaction. The catalyst added to the first mixed solution to facilitate the click chemistry reaction may be copper (Cu), ruthenium (Ru), and/or silver (Ag). The copper catalyst added to facilitate the click chemistry reaction may be, for example, monovalent copper ions (Cu(I)). To supply the monovalent copper ions, copper(I) bromide (CuBr) or copper(I) iodide (CuI) may be used. To supply the monovalent copper ions, a mixture of copper sulfate ($CuSO_4$) and sodium ascorbate (i.e., a reducing agent) may be used. In addition, to increase the yield of the click chemistry reaction, a stabilizing ligand may be added in combination with the copper catalyst to the first mixed solution. The stabilizing ligand may be, for example, tris-(benzyltriazolylmethyl)amine (TBTA).

The click chemistry reaction catalyzed by the monovalent copper ions may cause the first functional group and the third functional group to form triazole, i.e., the second compound. In FIG. 6A, the first carbon nanotubes 122 are bonded to the substrate 200 by the triazole. In addition, in FIG. 6B, the process in which the triazole is formed by a chemical reaction between the alkyne group (i.e., the first functional group) and the azide group (i.e., the third functional group) is illustrated. The triazole formed by the click chemistry reaction may be, for example, 1,2,3-triazole.

The click chemistry reaction between the first functional group and the third functional group causes some of the first carbon nanotubes 122 contained in the first mixed solution to bond to the substrate 200. However, the second carbon nanotubes 124 remain in the first mixed solution. Therefore, only the first carbon nanotubes 122 can be separated from the first mixed solution of the first carbon nanotubes 122 and the second carbon nanotubes 124.

If the above process is performed repeatedly, substantially all of the first carbon nanotubes 122 contained in the first mixed solution may be bonded to the substrate 200 and thus separated from the first mixed solution. If metallic carbon nanotubes and semiconducting carbon nanotubes are mixed in the first mixed solution, the metallic carbon nanotubes may be bonded to the substrate 200 by the click chemistry reaction and thus separated from the first mixed solution. Therefore, only the semiconducting carbon nanotubes are left in the first mixed solution.

The method of separating metallic carbon nanotubes from semiconducting carbon nanotubes using the click chemistry reaction provide the following effects.

Efforts to separate metallic carbon nanotubes from semiconducting carbon nanotubes have been continuously made since the discovery of carbon nanotubes. Examples of the method of separating carbon nanotubes include centrifugation, gel chromatography, and electrophoresis. The method of separating carbon nanotubes using centrifugation requires a high production cost because the equipment for centrifugation is expensive and only a small quantity of carbon nanotubes can be separated at a time. The method of separating carbon nanotubes using gel chromatography has a problem in that separated carbon nanotubes have low purity. In addition, the method of separating carbon nanotubes using electrophoresis is low in efficiency.

However, in the method of separating carbon nanotubes using the click chemistry reaction introduced in the present disclosure, a large quantity of highly pure metallic carbon nanotubes can be separated at a low production cost. This is because the method of separating carbon nanotubes according to the present disclosure does not use high-priced equipment such as a centrifuge and induces carbon nanotubes to react in large quantities in a solution state. In addition, since a reaction between certain functional groups is used, the purity of separated metallic carbon nanotubes is high.

The present disclosure will now be described in further detail with reference to the following example. This example is for illustrative purposes only, and is not intended to limit the scope of the present disclosure.

First, metallic carbon nanotubes having an alkyne group are formed. To this end, alkynephenyldiazonium salt having the alkyne group bonded at the position of a para-substituent is prepared. In addition, a first mixed solution of metallic and semiconducting carbon nanotubes is prepared. The concentration of carbon nanotubes in the first mixed solution may be 0.005 wt %. A carbon nanotube dispersant may further be added to the first mixed solution to uniformly mix the carbon nanotubes. In the current example, the carbon nanotube dispersant may be sodium cholate.

The alkynephenyldiazonium salt is added to the first mixed solution of the metallic carbon nanotubes and the semiconducting carbon nanotubes. The concentration of the alkynephenyldiazonium salt added to the first mixed solution may be 0.196 mM.

Figure 7:
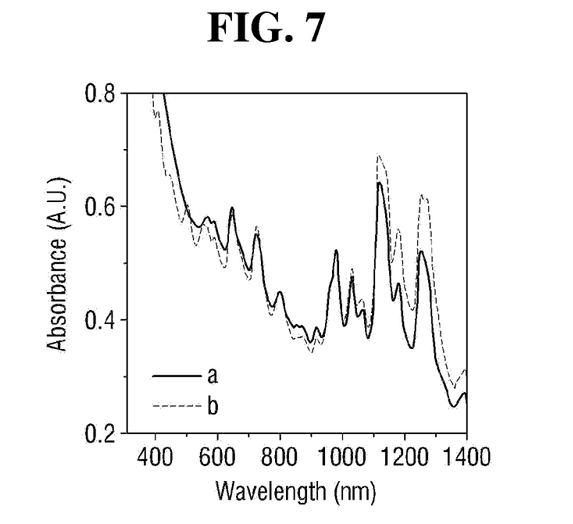
FIG. 7 is a graph illustrating the absorbance of a mixed solution of metallic carbon nanotubes and semiconducting carbon nanotubes when alkynephenyldiazonium salt was added to the mixed solution.

FIG. 7 is a graph illustrating the absorbance of the first mixed solution of the metallic carbon nanotubes and the semiconducting carbon nanotubes when the alkynephenyldiazonium salt was added to the first mixed solution. That is, FIG. 7 is a graph illustrating whether the alkyne group has been bonded to the metallic carbon nanotubes by the addition of the alkynephenyldiazonium salt to the first mixed solution. In FIG. 7, a is a graph of the absorbance of the first mixed solution having the alkynephenyldiazonium salt added therein, and b is a graph of the absorbance of the first mixed solution without the alkynephenyldiazonium salt. Referring to FIG. 7, light absorption is not present in a wavelength range of 450 to 550 nm. Since the wavelength range of 450 to 550 nm is a light absorption range of the metallic carbon nanotubes, it can be understood from FIG. 7 that the metallic carbon nanotubes contained in the first mixed solution reacted with the alkynephenyldiazonium salt.

Next, a substrate having an azide group attached thereto is fabricated. To this end, a PEI aqueous solution is prepared by mixing 2 wt % of PEI and 0.5 M of sodium chloride (NaCl) in DI water. In addition, a PAA-azide aqueous solution is prepared by mixing 5 wt % of polyacrylic acid, 5 wt % of azide, and 0.5 M of NaCl in the DI water.

A glass substrate is immersed in the PEI aqueous solution. As a result, an adhesive layer containing PEI is formed on the glass substrate.

The glass substrate having the adhesive layer is immersed in the PAA-azide aqueous solution. As a result, an active layer containing PAA is formed on the adhesive layer, and the azide group is attached onto the active layer. That is, the azide group is bonded onto the glass substrate.

To separate the metallic carbon nanotubes from the semiconducting carbon nanotubes by bonding the metallic carbon nanotubes to the glass substrate, the glass substrate having the azide group bonded to a surface thereof is immersed in the first mixed solution of the semiconducting carbon nanotubes and the metallic carbon nanotubes having the alkyne group. Here, monovalent copper ions are added as a catalyst to facilitate a click chemistry reaction between the alkyne group and the azide group. To supply the monovalent copper ions, copper(I) bromide is added to the first mixed solution. In addition, TBTA is additionally added to the first mixed solution in order to stabilize the monovalent copper ions.

The click chemistry reaction that occurs between the azide group and the alkyne group causes the metallic carbon nanotubes contained in the first mixed solution to bond to the glass substrate. Therefore, the metallic carbon nanotubes are separated from the semiconducting carbon nanotubes.

Figure 8:
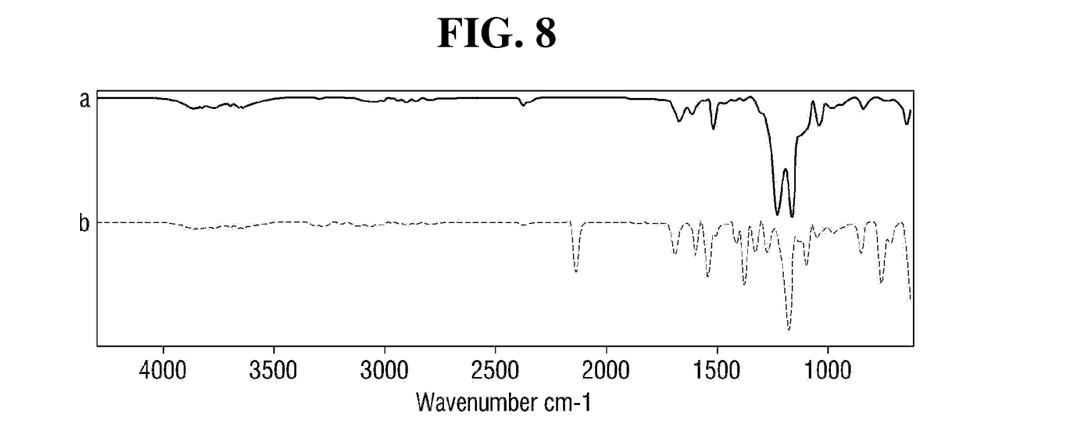
FIG. 8 is an infrared spectrum graph showing the occurrence of a click chemistry reaction between an alkyne group and an azide group.

FIG. 8 is an infrared spectrum graph showing the occurrence of the click chemistry reaction between the alkyne group and the azide group. In FIG. 8, a is a graph of the infrared spectrum of the glass substrate taken out from the first mixed solution after the glass substrate having the azide group bonded to the surface thereof was immersed in the first mixed solution of the semiconducting carbon nanotubes and the metallic carbon nanotubes having the alkyne group. In addition, b is a graph of the infrared spectrum of the glass substrate having the azide group bonded to the surface thereof. It can be understood from FIG. 8 that the click chemistry reaction between the alkyne group and the azide group was successful.

In concluding the detailed description, those skilled in the art will appreciate that many variations and modifications can be made to the preferred embodiments without substantially departing from the principles of the present disclosure. Therefore, the disclosed preferred embodiments of the invention are used in a generic and descriptive sense only and not for purposes of limitation.

What is claimed is:

1. A method of separating carbon nanotubes, the method comprising:
    forming first carbon nanotubes having a first functional group;
    forming a substrate having a second functional group;
    adhering the first carbon nanotubes to the substrate by a click chemistry cycloaddition reaction between the first functional group and the second functional group; and
    wherein the first functional group is an alkyne functional group, and the second functional group is an azide functional group.

2. A method of separating carbon nanotubes, the method comprising:
    forming a first mixture of metallic carbon nanotubes and semiconducting carbon nanotubes;
    attaching an alkyne functional group to the metallic carbon nanotubes by adding a first compound to the first mixture;
    forming a substrate having an azide functional group attached thereto; and
    causing the metallic carbon nanotubes to be bonded to the substrate by triazole formed by a chemical reaction between the alkyne functional group and the azide functional group.

3. The method of claim 2, wherein the first compound contains alkynephenyldiazonium salt.

4. The method of claim 2, wherein the forming of the substrate having the azide functional group attached thereto comprises preparing a mixed solution of the azide functional group and a polymer compound, forming an active layer on a bare substrate by immersing the bare substrate in the mixed solution, and letting the azide functional group bond onto the active layer.

5. A method of separating semiconducting carbon nanotubes from metallic carbon nanotubes, the method comprising:
    providing a mixed solution including metallic carbon nanotubes and semiconducting carbon nanotubes, wherein an alkyne functional group is attached to the metallic carbon nanotubes;
    providing a substrate having an azide functional group; and
    making the substrate having the azide functional group in contact with the mixture solution to cause a click chemistry reaction between the azide functional group and the alkyne functional group.

6. The method of claim 5, wherein the click chemistry reaction between the azide functional group and the alkyne functional group produces triazole, and wherein the metallic carbon nanotubes are attached to the substrate by triazole, thereby separating the semiconducting carbon nanotubes from the metallic carbon nanotubes.

7. The method of claim 5, wherein the alkyne functional group is connected to the metallic carbon nanotubes via another compound.

8. The method of claim 5, wherein the alkyne functional group is directly connected to the metallic carbon nanotubes.

* * * * *